(12) United States Patent
Reed

(10) Patent No.: US 6,234,327 B1
(45) Date of Patent: May 22, 2001

(54) SUTURE HOLDER

(76) Inventor: Lisa Reed, #2 Old Landing Rd., Mantua, NJ (US) 08051

( * ) Notice: Subject to any disclaimer, the term of this patent is extended or adjusted under 35 U.S.C. 154(b) by 0 days.

(21) Appl. No.: 09/497,259

(22) Filed: Feb. 3, 2000

(51) Int. Cl.[7] ....................................... A47F 7/00
(52) U.S. Cl. .................... 211/85.13; 211/85.15; 211/120; 206/363; 206/63.3
(58) Field of Search ................. 211/85.13, 120, 211/85.15, 89.01, 45; 206/363, 63.3

(56) References Cited

U.S. PATENT DOCUMENTS

| | | |
|---|---|---|
| 79,776 | 7/1868 | Rand . |
| 780,443 | 1/1905 | Phillips . |
| 1,248,760 | 12/1917 | Wallin . |
| 2,588,589 | 3/1952 | Tauber ................... 223/109 |
| 3,819,039 | 6/1974 | Erickson ............... 206/388 |
| 4,415,089 | 11/1983 | Ruffa ....................... 211/13 |
| 4,545,489 | 10/1985 | Welch ..................... 211/11 |
| 5,282,533 * | 2/1994 | Holzwarth et al. ....... 206/63.3 |
| 5,335,775 * | 8/1994 | Scanlon et al. ........... 206/63.3 |
| 5,848,714 | 12/1998 | Robson ................... 211/170 |

* cited by examiner

Primary Examiner—Robert W. Gibson, Jr.
(74) Attorney, Agent, or Firm—John H. Scarborough; Robert R. Mallinckrodt

(57) ABSTRACT

A suture holder allows a scrub nurse to "load" (i.e., retrieve a suture needle and thread onto a surgical needle driver) with one hand during a surgical operation. The suture holder is made of spring loops arranged on a supporting base to hold suture packets. Leaf springs can also be employed on a suture holder to hold and secure suture packets during surgery.

24 Claims, 3 Drawing Sheets

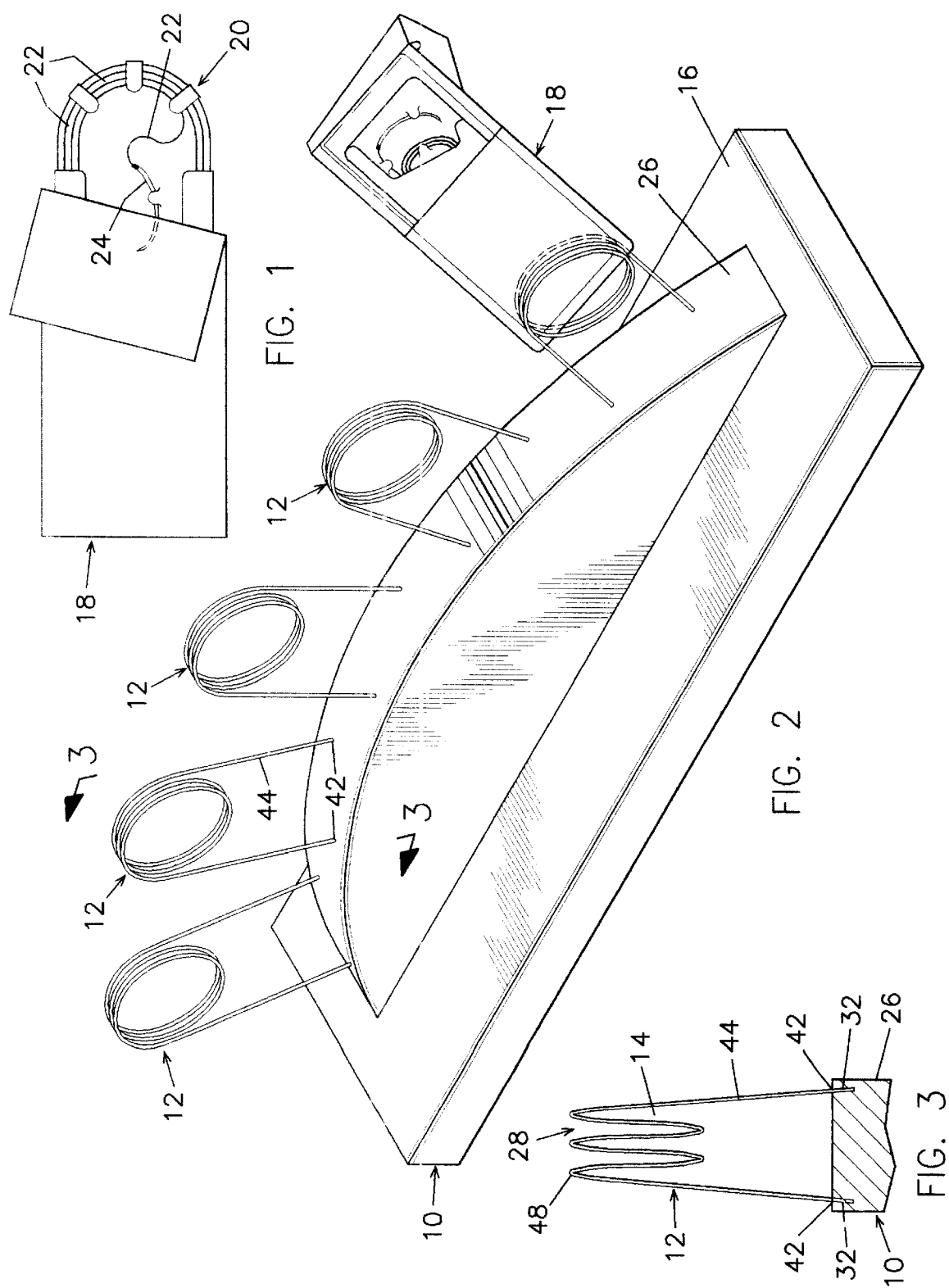

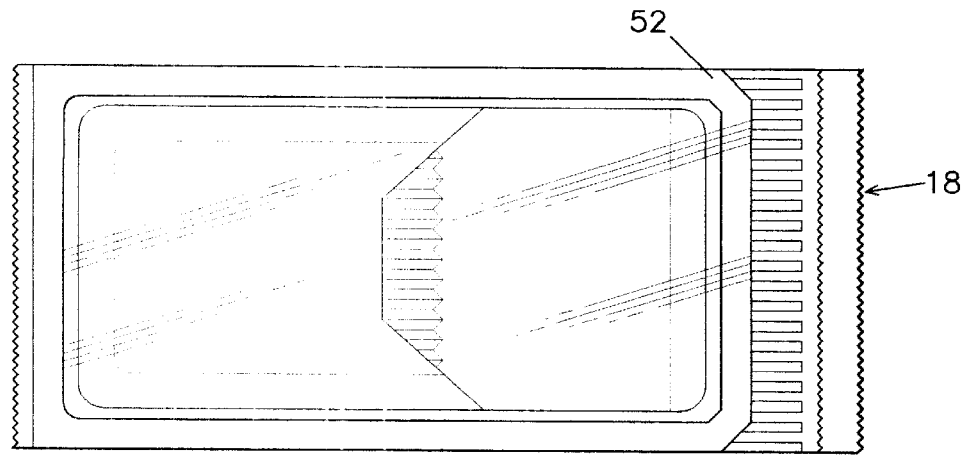
FIG. 9
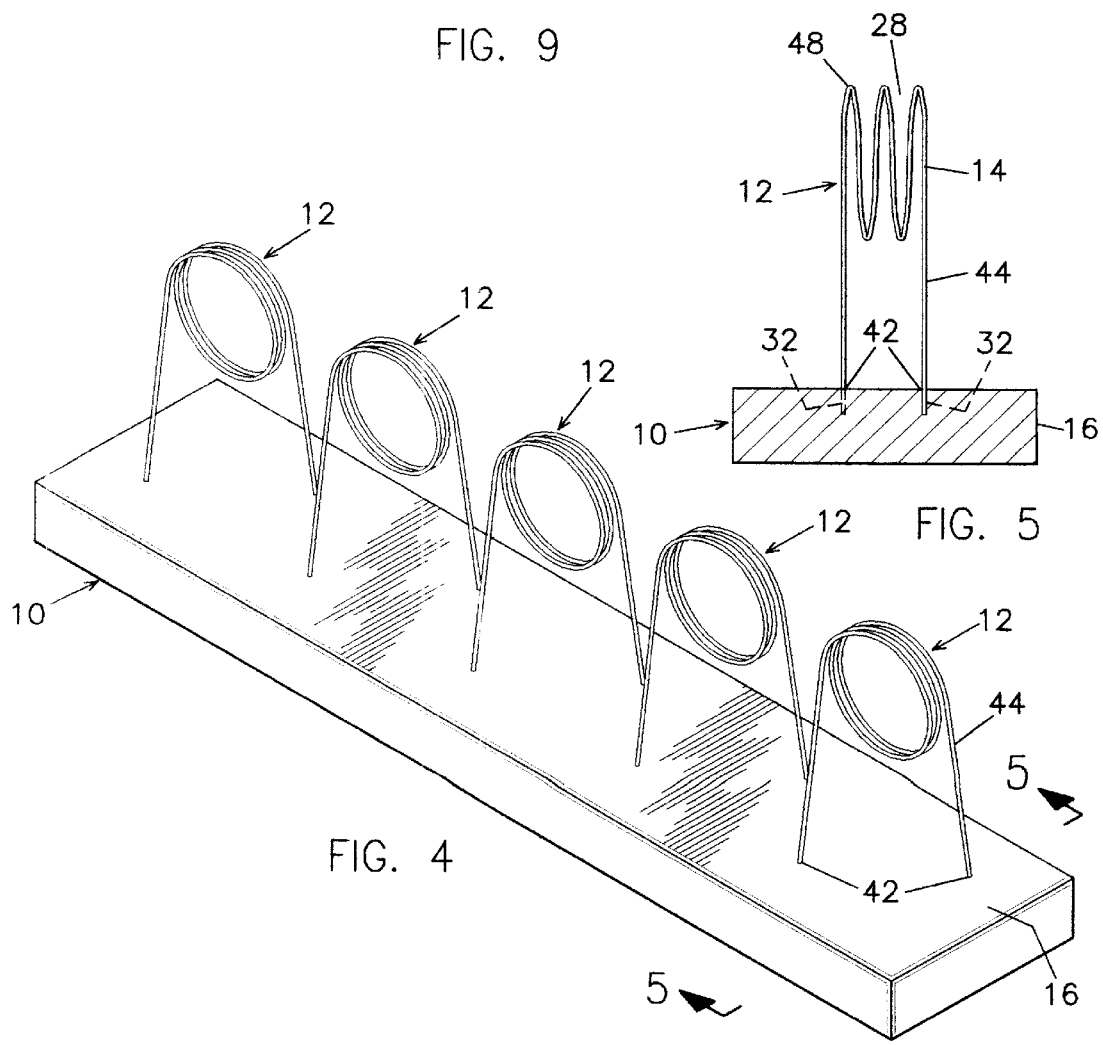
FIG. 5
FIG. 4

SUTURE HOLDER

BACKGROUND OF THE INVENTION

1. Field

This invention is in the field of devices for holding suture packs during a surgical operation.

2. State of the Art

During an operation, surgical assistants, or scrub nurses, must act quickly and with precision. With regard to handling sutures (i.e., surgical threads) used to bind surgical incisions, presently suture packets, or envelopes, are arranged on a sterile field (i.e., sterile table). When sutures are needed, currently a surgical assistant, or scrub nurse, must use both hands to select the proper suture from the table, open the suture packet, then extract, load, and pass the suture thread to a surgeon.

Some prior art provide for suture holders in connection with surgical procedures: Robson U.S. Pat. No. 5,848,714 provides a suture rack with interlocking trays with compartments containing leaf spring clips to hold suture packets. The trays are supported on a base where trays can lock together. Ruffa U.S. Pat. No. 4,415,089 is a suture and surgical accessory rack having a disposable sterile screen supported on a bar frame. The disposable sterile screen has pockets which can hold sutures, needles, and scissors. Erickson U.S. Pat. No. 3,819,039 is suture holder made of a resilient material having parallel slits formed by parallel abutments of the resilient material. Suture thread is held within the slits while suture needles are inserted into the abutments for temporary storage. Tauber U.S. Pat. No. 2,588,589 is a surgeon's prethreaded needle holder. The invention provides elongate members having grooved spaces for holding suture thread and spring-like members for holding prethreaded needles.

Wallin U.S. Pat. No. 1,248,760 is a towel rack that is structurally similar to the instant invention. Wallin provides a plurality of spring loops which are arranged in very close proximity to each other, even touching, thereby permitting towels to be inserted therebetween; the spring loops are mounted on a supporting board. Whereas in Wallin, towels are held between the loops; in this invention, the sutures are held within coils of spring loops. Whereas in Wallin, the spring loops are held in holes in the towel rack; in the instant invention, spring loops can be secured permanently in the base of the suture holder by means of a welded or soldered connection. Whereas in Wallin, the loops need not be formed into coils; in this invention, coils are absolutely needed to hold suture packets in place.

Other similar devices of the prior art are as follows: Welch U.S. Pat. No. 4,545,489 is a desk organizer where loops formed by metallic strips serves as a storage rack for letters and other papers. Phillips U.S. Pat. No. 780,443 is also a desk organizer where a coiled spring mounted on a supporting board holds papers and other accessories. Rand U.S. Pat. No. 79,776 is a whip holder, patented back in 1868. Rand also has loops formed by metallic strips in the shape of bows mounted on a supporting board. The whips are held in place between the metallic loops.

None of the prior art provides a suture holder that allows a scrub nurse to load and discard sutures with one hand and that is simple to use and, at the same time, inexpensive to manufacture.

OBJECTS OF THE INVENTION

The primary object of this invention is to provide a suture holder which allows a scrub nurse to load and discard sutures using only one hand.

Another object of this invention is to provide a suture holder which is easy and simple to use.

Further, it is an object to provide a suture holder which is inexpensive to manufacture.

Still further, it is an object to keep the flow of the operation going efficiently and precisely optimizing the activities of the surgical team working together thereby enhancing the quality of care of the patient.

SUMMARY OF THE INVENTION

The suture holder of this invention is comprised of a supporting base onto which several spring loops or other such devices are attached. The spring loops hold suture packets of various size sutures during a surgical operation. In addition to spring loops, leaf springs can be employed to hold suture packets in place.

The base and spring loops can be made of stainless steel which can be made sterile by means of an autoclave prior to surgery, or the base and loops can be made of plastic which can be made surgically sterile before they are unpackaged prior to surgery. Plastic suture holders need a temporary adhesive applied to the bottom thereof in order to hold the suture holder in place while the scrub nurse loads a suture onto a needle driver.

BRIEF DESCRIPTION OF THE DRAWINGS

The best mode presently contemplated for carrying out the invention in actual practice is shown in the accompanying drawings, in which:

FIG. 1 is a top plan view of a representative suture packet (manufactured by Ethicon, Inc. shown), unwrapped and opened.

FIG. 2 is a perspective view of a suture holder.

FIG. 3 is a vertical section of the suture holder taken along 3—3 of FIG. 2, with a spring loop shown in elevation.

FIG. 4 is a perspective view of another embodiment of the suture holder.

FIG. 5 is a vertical section of the suture holder taken along 5—5 of FIG. 4, with the spring loop shown in elevation.

FIG. 9 is a top plan view of another representative suture packet (manufactured by U.S. Surgical, Inc. shown) wrapped in clear cellophane.

DETAILED DESCRIPTION OF THE ILLUSTRATED EMBODIMENT

Figures 6, 7, 8:
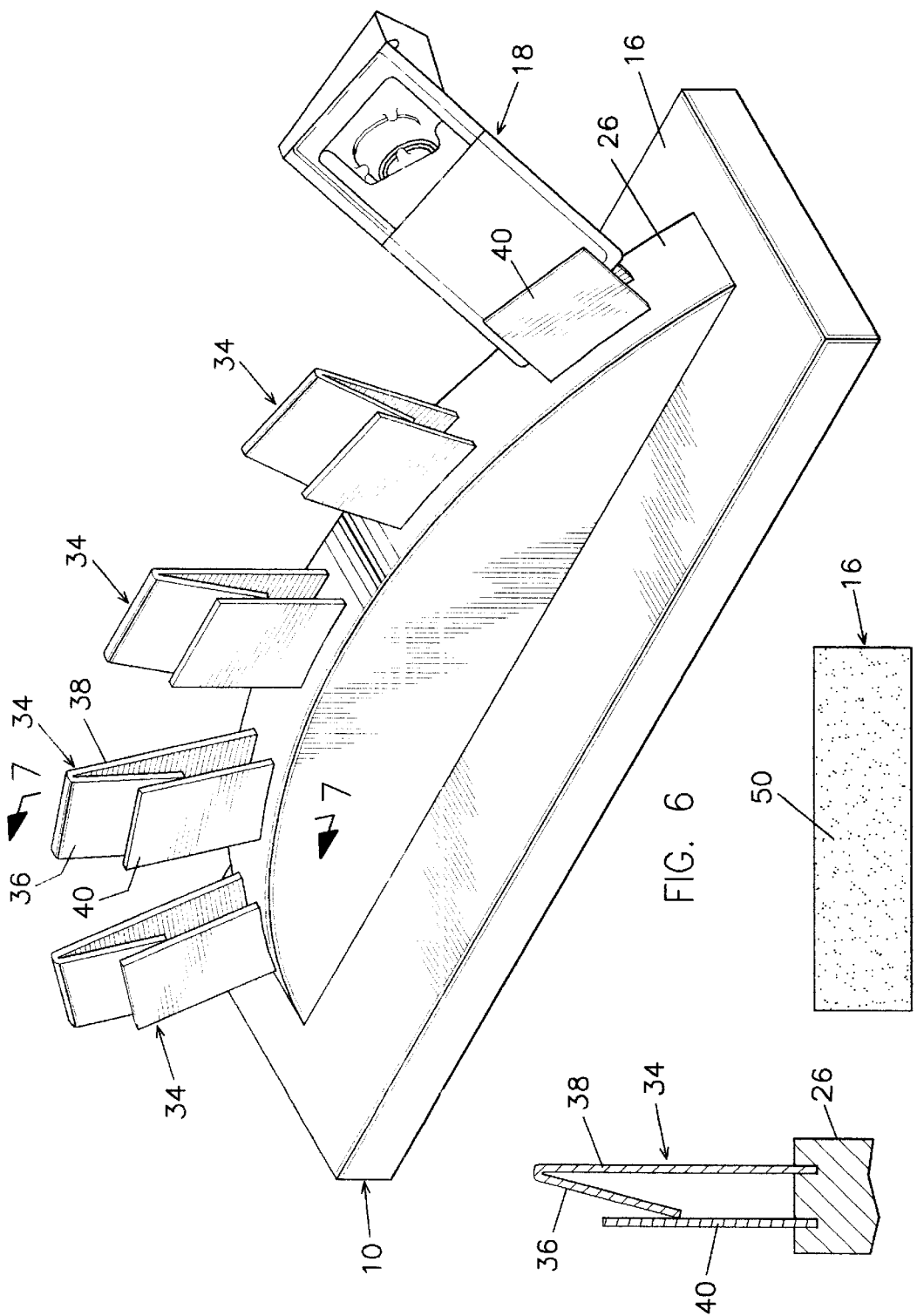
FIG. 6 is a perspective view of still another embodiment of the suture holder using leaf springs to hold suture packets.
FIG. 7 is a side section of a leaf spring device taken along 7—7 of FIG. 6.
FIG. 8 is a bottom plan view of the base of the suture holder showing a temporary adhesive applied to the bottom thereof.

In order to illustrate how the invention operates, FIG. 1 shows a typical suture packet 18 opened to expose its contents. A typical suture packet contains a frame 20 around which suture thread 22 is wound. A suture needle 24, attached to the suture thread 22 is also secured to the frame 20.

In the illustrated embodiment, FIG. 2 shows the suture holder 10 having a plurality of spring loops 12 mounted on an arched platform 26 which itself is mounted on a supporting base 16. Spring loops 12 are spaced sufficiently apart so that suture packets 18 may be inserted and withdrawn with ease.

FIG. 3 shows a single spring loop 12 mounted on the arched platform 26 of the base 16. A wire 44 is spirally wound into coils which form loops 14 of the spring loops 12. A loop 14 can be described as having a loop-top 48 with insertion slots 28 formed between loops 14 into which a suture packet is inserted and held during surgery. The ends 42 of the wire 44, extending away from the coils or loops 14, are inserted into spaced openings 32 of the arched platform 26 to form a spring loop 12 as shown in FIGS. 2 and 3. Ends 42 of spring loops 12 can be permanently attached to the arched platform 26 inside the spaced openings 32 by means of a welded or soldered connection, FIG. 3 where the arched platform 26 is made of a high-density metal. However, where the arched platform 26 is made of a plastic material, ends 42 of spring loops 12 can be permanently glued inside the spaced openings 32. Where ends 42 of spring loops 12 are attached to the supporting base 16 itself, a similar construction can be effected, FIG. 5.

FIG. 2 also shows how coils or loops 14 hold suture packets 18, i.e., by inserting the suture packet 18 into an insertion slot 28 (not marked) between the loop-tops 48 of adjacent coils of the spring loop 12. The spring loops 12, arched platform 26, and supporting base 16 can be described as a rack.

FIG. 3 shows spaced openings 32 drilled into the arched platform 26 at an angle to the perpendicular. This is done so that when the ends 42 of the wire 44, which form a spring loop 12, are inserted into the spaced openings 32, the tension of the loops 14 against each other will provide greater holding strength to secure suture packets. FIG. 3 also shows the spring loop having three loop-tops 48 having two insertion slots 28 into which a suture packet can be inserted. The holding strength of a spring loop can be effected by the number of loops forming the spring loop. It is preferable that a spring loop have four loops, i.e., having three insertion slots. However, a spring loop can be formed with any number of loops. Thickness of the wire will also affect the holding strength of spring loops. Therefore, the angle at which spaced openings are to be drilled into the platform, the number of loops, and the thickness of the wire should all be adjusted such that the holding strength of the spring loops 12 be sufficient to hold a suture packet 18 in place while a scrub nurse extracts a suture with one hand but still to allow the scrub nurse to be able to insert a suture packet 18 easily into an insertion slot 28.

FIG. 4 shows another embodiment in which the spring loops 12 are mounted directly onto the base 16 of the suture holder 10.

FIG. 5 shows another embodiment of the spring loop 12 which are inserted at a perpendicular angle to the base 16 of the suture holder 10 taken along 5—5 of FIG. 4. Ends 42 of spring loop 12 are inserted perpendicularly into space openings 32 of base 16, FIG. 5. It should be understood this invention contemplates that either structure of the spring loops (i.e., FIGS. 3 and 5) be incorporated with either of the suture holders, FIGS. 2 or 4 (i.e., a suture holder having an arched platform or not having an arched platform). However, the use of an arched platform would allow greater spacing between spring loops within a smaller area.

Instead of spring loops, leaf springs 34, or clamps, can be used to hold suture packets 18 in place, FIG. 6 which illustrates another embodiment of this invention. Section 7—7 cuts a leaf spring 34 revealing a side section thereof, FIG. 6. A leaf spring 34 is comprised of a spring clip 36 held onto a back support 38 and a front retainer 40. When in use, a suture packet slides between the spring clip 36 and the front retainer 40 to be held in place during surgery. Leaf springs 14 are attached to the arched platform 26 by means of a welded or soldered connection. The leaf springs 34, arched platform 26, and supporting base 16 can be described as a rack.

Both FIGS. 2 and 6 show unwrapped suture packets being held by suture holders 10; in FIG. 2 the suture packet 18 is being held by spring loop 12 while in FIG. 6 the suture packet is being held by a leaf spring 34.

It is contemplated that a suture holder, including the supporting base and an arched platform, can be constructed of stainless steel, of any high-density metal, of plastic, or of any other appropriate material. A stainless steel suture holder could be sterilized in an autoclave between surgeries, but plastic suture holders would be disposable. A stainless steel suture holder should be heavy enough to allow a scrub nurse to extract a suture with one hand. However, a plastic suture holder would need to have a temporary adhesive applied to the bottom of its base in order to provide the resistance necessary to allow a scrub nurse to extract a suture with one hand. FIG. 8 shows the bottom of the supporting base 16 of a plastic suture holder with temporary adhesive 50 applied.

During surgery, sutures are applied to an incision or open wound by means of a "needle driver". A needle driver is a tool somewhat similar to pliers that has a ratcheting mechanism which both holds a suture needle in place while allowing the user to thread the needle to close and bind an incision or open wound. A suture is said to be "loaded" when the needle driver has picked up the suture needle and holds the suture needle, by means of the ratcheting mechanism.

Prior to surgery, a box of sutures packets 18 is delivered to an operating room, under non-sterile conditions by a circulating nurse (i.e., one who is not scrubbed to a sterile condition). Typically, suture packets are contained in boxes of approximately twenty (20). Each packet is contained in a clear outer wrap 52, such as cellophane, FIG. 9. FIG. 9 also shows a wrapped suture packet 18 still packaged within the clear outer wrap 52. Sutures are packed in boxes under sterile conditions. The packet itself is made of aluminum foil or cardboard envelope. The circulating nurse opens the box and opens the clear outer wrap of the suture packet. Either the circulating nurse exposes the suture packet 18 (envelope) so it can be plucked out by the scrub nurse, or the circulating nurse deposits the suture packet 18 onto the sterile field (or sterile table) for each suture that is needed, FIGS. 1 and 9. The circulating nurse who opens the box does not touch (or otherwise contaminate) the suture packets.

The suture packet has writing on the outside which identifies the type and size of the suture (i.e., thread) inside. Inside the suture packet 18 is contained a frame 22, usually made of plastic, onto which the suture thread 22 is wound and held in place, FIG. 1. The suture thread 22 is said to be "swedged" (i.e., bonded) to a suture needle 24, which is held in place by a notch on the plastic frame, FIG. 1.

Prior to use, the scrub nurse opens the suture packets 18 (envelopes), exposing the frame within, then places the opened suture packets 18 in the suture holder 10 under sterile conditions, FIGS. 2 and 4. FIG. 9 shows flap 54 which the scrub nurse would remove in order to open the suture packet 18, manufactured by U.S. Surgical, Inc. The sutures are now ready to allow the scrub nurse to withdraw and load a suture needle with one hand from the frame during a surgical operation. It should be noted FIG. 1 shows a suture packet 18 manufactured by Ethicon, Inc. while FIGS. 2, 6, and 9 show suture packets 18 manufactured by U.S. Surgical, Inc.

While the present invention has been disclosed in connection with the preferred embodiment thereof, it should be understood that there may be other embodiments which fall within the spirit and scope of the invention as defined by the following claims.

I claim:

1. A method for holding suture packets so that the contents of the suture packets are available for the purpose of loading a suture onto a needle driver using only one hand, comprising the steps of:
   opening at least one suture packet in a sterile environment;
   obtaining a rack having
      a supporting base,
      a plurality of spaced openings drilled into the supporting base, and
      a plurality of spring loops, each spring loop comprised of a wire spirally wound into a multiplicity of coils spaced to form insertion slots between adjacent coils adapted to receive and hold suture packets with ends of said wire extending away from said coils and inserted into a pair of openings of the plurality of spaced openings, said wires each forming a said spring loop; and
   placing said opened suture packets into selected insertion slots of selected spring loops whereby the opened suture packets are held by the rack with contents of the opened suture packet available to be removed by one hand from the opened suture packets.

2. A suture holder, comprising:
   a supporting base;
   an arched platform attached to the supporting base;
   a plurality of spaced openings drilled into said arched platforms; and
   a plurality of spring loops, each spring loop comprised of a wire spirally wound into a multiplicity of coils spaced to form insertion slots between adjacent coils adapted to receive and hold suture packets with ends of said wire extending away from said coils and inserted into a pair of openings of the plurality of spaced openings, said wires each forming a said spring loop.

3. A method for holding suture packets as defined by claim 1, wherein the step of obtaining a rack includes obtaining a rack having the spaced openings drilled at an angle to the perpendicular into the supporting base.

4. A method for holding suture packets as defined by claim 1, wherein the step of obtaining a rack includes obtaining a rack having the spaced openings drilled perpendicularly into the supporting base.

5. A suture holder according to claim 2, wherein the spaced openings are drilled at an angle to the perpendicular into the supporting base.

6. A suture holder according to claim 2, wherein the spaced openings are drilled perpendicularly into the supporting base.

7. A method for holding suture packets as defined by claim 1, wherein the step of obtaining a rack includes obtaining a rack having the supporting base constructed of a high-density metal.

8. A suture holder according to claim 2, wherein the arched platform and supporting base are constructed of a high-density metal.

9. A method for holding suture packets as defined by claim 7, wherein in the step of obtaining a rack includes obtaining a rack having the high-density metal as stainless steel.

10. A suture holder according to claim 8, wherein the high-density metal is stainless steel.

11. A suture holder according to claim 8, wherein the arched platform is attached to the supporting base by a welded connection.

12. A suture holder according to claim 8, wherein the arched platform is attached to the supporting base by a soldered connection.

13. A method for holding suture packets as defined by claim 7, wherein in the step of obtaining a rack includes obtaining a rack having the ends of the wires of the spring loops secured permanently within the spaced openings of the supporting base by a welded connection.

14. A method for holding suture packets as defined by claim 7, wherein in the step of obtaining a rack includes obtaining a rack having the ends of the wires of the spring loops secured permanently within the spaced openings of the supporting base by a soldered connection.

15. A suture holder according to claim 8, wherein the ends of the wires of the spring loops are secured permanently within the spaced openings of the arched platform by a welded connection.

16. A suture holder according to claim 8, wherein the ends of the wires of the spring loops are secured permanently within the spaced openings of the arched platform by a soldered connection.

17. A method for holding suture packets as defined by claim 1, wherein in the step of obtaining a rack includes obtaining a rack having the supporting base constructed of a plastic material.

18. A suture holder according to claim 2, wherein the arched platform and supporting base are constructed of a plastic material.

19. A suture holder according to claim 18, wherein the arched platform is attached to the supporting base by glue.

20. A method for holding suture packets as defined by claim 17, wherein in the step of obtaining a rack includes obtaining a rack having the ends of the wires of the spring loops secured permanently within the spaced openings of the supporting base by glue.

21. A suture holder according to claim 18, wherein the ends of the wires of the spring loops are secured permanently within the spaced openings of the arched platform by glue.

22. A method for holding suture packets as defined by claim 17, wherein in the step of obtaining a rack includes obtaining a rack having a temporary adhesive material applied to the bottom of the supporting base.

23. A suture holder according to claim 18, wherein a temporary adhesive material is applied to the bottom of the supporting base.

24. A method for loading a suture onto a needle driver using only one hand, comprising the steps of:
   opening suture packets, in a sterile environment;
   obtaining a rack having
      a supporting base,
      a plurality of spaced openings drilled into the supporting base, and
      a plurality of spring loops, each spring loop comprised of a wire spirally wound into a multiplicity of coils spaced to form insertion slots between adjacent coils adapted to receive and hold suture packets with ends of said wire extending away from said coils and inserted into a pair of openings of the plurality of spaced openings, said wires each forming a said spring loop,
   placing said opened suture packets into selected insertion slots of selected spring loops whereby the opened suture packets are held by the rack with contents of the opened suture packet available to be removed by one hand from the opened suture packets; and
   loading selected sutures with one hand from selected said opened suture packets as needed during a surgical operation.

* * * * *